United States Patent
Aluru et al.

(10) Patent No.: US 11,805,968 B2
(45) Date of Patent: Nov. 7, 2023

(54) INTRAOPERATIVE ENDOSCOPE CLEANING SYSTEM

(71) Applicant: BAYOU SURGICAL, INC., Houston, TX (US)

(72) Inventors: Rajitha Aluru, Houston, TX (US); William Cohn, Houston, TX (US); Jorge Salazar, Houston, TX (US); Scott Sloss, Houston, TX (US); Abdul Umaru, Houston, TX (US)

(73) Assignee: Bayou Surgical, Inc., Houston, TX (US)

( * ) Notice: Subject to any disclaimer, the term of this patent is extended or adjusted under 35 U.S.C. 154(b) by 776 days.

(21) Appl. No.: 16/690,996

(22) Filed: Nov. 21, 2019

(65) Prior Publication Data

US 2021/0127964 A1    May 6, 2021

Related U.S. Application Data

(60) Provisional application No. 62/930,983, filed on Nov. 5, 2019.

(51) Int. Cl.
| | | |
|---|---|---|
| *A61B 1/12* | (2006.01) | |
| *A61L 2/16* | (2006.01) | |
| *A61B 17/34* | (2006.01) | |

(52) U.S. Cl.
CPC ............ *A61B 1/126* (2013.01); *A61B 17/34* (2013.01); *A61B 17/3417* (2013.01); *A61L 2/16* (2013.01);

(Continued)

(58) Field of Classification Search
CPC ..... A61B 1/126; A61B 1/00006; A61B 1/015; A61B 17/34; A61B 17/3417;
(Continued)

(56) References Cited

U.S. PATENT DOCUMENTS

| | | |
|---|---|---|
| 2,264,746 A | 12/1941 | Ellwood |
| 4,635,949 A | 1/1987 | Lucas et al. |

(Continued)

FOREIGN PATENT DOCUMENTS

| | | |
|---|---|---|
| CA | 2842217 A1 | 3/2008 |
| CN | 1905832 A | 1/2007 |

(Continued)

OTHER PUBLICATIONS

Amazon.com: Morris Products 70332 Roller Ball Contacts, Open, Circuit . . . , http://www.amazon.com/Morris-Products-70332-Contacts-Circuit/dp/B . . . , downloaded Mar. 16, 2016, 8 pages.

(Continued)

*Primary Examiner* — Nathan R Price
*Assistant Examiner* — Justin L Zamory

(57) ABSTRACT

Apparatus, systems, and methods for cleaning an endoscope during a procedure, are disclosed. One method comprises utilizing a trocar comprising a main body defining a cavity for receiving an endoscope, a wash orifice disposed in the main body and configured allow a flow of wash solution into the cavity, and a gas orifice disposed between the distal end of the main body and the wash orifice, the gas orifice configured allow a flow of gas into the cavity, the method comprising: washing the endoscope; drying the endoscope; and managing residual fluids on the endoscope or in the cavity, or both.

25 Claims, 9 Drawing Sheets

(52) U.S. Cl.
CPC ... *A61B 2562/0257* (2013.01); *A61L 2202/24* (2013.01)

(58) Field of Classification Search
CPC . A61B 17/3421; A61B 17/3478; A61B 90/70; A61M 3/00; A61M 25/003; A61M 25/0015; A61M 2025/0019; B08B 3/02
See application file for complete search history.

(56) References Cited

U.S. PATENT DOCUMENTS

| | | | |
|---|---|---|---|
| 4,800,869 | A | 1/1989 | Nakajima |
| 4,852,551 | A | 8/1989 | Opie et al. |
| 5,274,874 | A | 1/1994 | Cercone et al. |
| 5,386,817 | A | 2/1995 | Jones |
| 5,429,596 | A | 7/1995 | Arias et al. |
| 5,476,447 | A | 12/1995 | Noda et al. |
| 5,573,494 | A | 11/1996 | Yabe et al. |
| 5,575,756 | A | 11/1996 | Karasawa et al. |
| 5,697,888 | A | 12/1997 | Kobayashi et al. |
| 6,126,592 | A | 10/2000 | Proch et al. |
| 6,126,593 | A | 10/2000 | Honda et al. |
| 7,771,384 | B2 | 8/2010 | Ravo |
| 8,057,443 | B2 | 11/2011 | McNeil |
| 8,672,890 | B2 | 3/2014 | Franer et al. |
| 8,690,764 | B2 | 4/2014 | Clark et al. |
| 8,690,831 | B2 | 4/2014 | Duke |
| 8,915,842 | B2 | 12/2014 | Weisenburgh et al. |
| 9,211,059 | B2 | 12/2015 | Drach et al. |
| 11,583,176 | B2 | 2/2023 | Aluru et al. |
| 2005/0077689 | A1 | 4/2005 | Hueil |
| 2006/0161045 | A1 | 7/2006 | Merril et al. |
| 2006/0293559 | A1 | 12/2006 | Grice, III et al. |
| 2007/0282253 | A1 | 12/2007 | Sasaki |
| 2008/0255424 | A1 | 10/2008 | Durgin et al. |
| 2009/0253966 | A1 | 10/2009 | Ichimura |
| 2009/0270818 | A1 | 10/2009 | Duke |
| 2009/0312783 | A1 | 12/2009 | Whayne et al. |
| 2011/0152776 | A1 | 6/2011 | Hartoumbekis et al. |
| 2012/0022331 | A1 | 1/2012 | Poll et al. |
| 2013/0053643 | A1 | 2/2013 | Yoshida |
| 2014/0188038 | A1 | 7/2014 | Stearns et al. |
| 2014/0371763 | A1 | 12/2014 | Poll et al. |
| 2015/0190041 | A1* | 7/2015 | Su ............... A61B 1/127 600/109 |
| 2017/0078583 | A1 | 3/2017 | Haggerty et al. |
| 2018/0078120 | A1 | 3/2018 | Poll et al. |
| 2019/0125176 | A1* | 5/2019 | Burt ............... A61B 1/00006 |
| 2020/0163541 | A1 | 5/2020 | Holsten |
| 2020/0375444 | A1 | 12/2020 | Coffeen et al. |
| 2021/0127963 | A1 | 5/2021 | Aluru et al. |
| 2022/0192480 | A1 | 6/2022 | Burt et al. |

FOREIGN PATENT DOCUMENTS

| | | |
|---|---|---|
| CN | 101170941 A | 4/2008 |
| CN | 101296648 A | 10/2008 |
| CN | 101627894 A | 1/2010 |
| CN | 101668474 A | 3/2010 |
| CN | 202446249 U | 9/2012 |
| CN | 103957769 A | 7/2014 |
| CN | 104379045 A | 2/2015 |
| CN | 104720733 A | 6/2015 |
| CN | 204636289 U | 9/2015 |
| CN | 105310636 A | 2/2016 |
| EP | 2111808 A2 | 10/2009 |
| EP | 2886037 A1 | 6/2015 |
| JP | H07289501 A | 11/1995 |
| JP | 2009261948 A | 11/2009 |
| JP | 2013048821 A | 3/2013 |
| WO | WO-02100455 A2 | 12/2002 |
| WO | WO-2006039646 A2 | 4/2006 |
| WO | WO-2010046891 A2 | 4/2010 |
| WO | WO-2012066992 A1 | 5/2012 |
| WO | WO-2013012790 A2 | 1/2013 |
| WO | WO-2013183014 A1 | 12/2013 |
| WO | WO-2014050571 A1 | 4/2014 |
| WO | WO-2017184415 A1 | 10/2017 |
| WO | WO-2022235262 A1 | 11/2022 |

OTHER PUBLICATIONS

Communication—Extended European Search Report, European Patent Application No. 17786362.8, dated Jan. 13, 2020, 6 pages.
First Office Action, China Patent Application No. 2017800379560, dated Dec. 1, 2020, 8 pages.
Insinkerator, Food Waste Disposer, Sink Top Switch, downloaded Mar. 16, 2016, 2 pages.
International Search Report and Written Opinion for International Application No. PCT/US2021/030700 dated Jan. 25, 2022, 16 pages.
International Search Report and Written Opinion, International Patent Application No. PCT/US2017/027320, dated Jul. 17, 2017, 12 pages.
McKenna, D. et al., "A Novel Device Maintaining Clear Optics During Surgery", floshield.com/images/literature/Floshield-Lit_SAGES.pdf, downloaded May 23, 2019, 1 page.
MedGadget, ENDOPATH XCEL Trocar with OPTIVIEW Keeps The Lens Clean for Superior Visualization, http://www.medgadget.com/2010/03/endopath_xcel_trocar_with-optivie . . . , downloaded Mar. 16, 2016, 8 pages.
Non-Final Office Action for U.S. Appl. No. 16/690,979, dated Jul. 15, 2022, 20 pages.
Non-Final Office Action for U.S. Appl. No. 17/692,550, dated Aug. 31, 2022, 21 pages.
Notice of Reasons for Rejection, Japanese Patent Application No. 2018-555658, dated Jan. 20, 2021, 8 pages.
Office Action for Australian Application No. 2017253708, dated Mar. 18, 2022, 4 pages.
Office Action for Chinese Application No. 20178037956, dated Jun. 10, 2022, 16 pages.
Office Action issued in U.S. Appl. No. 16/094,754 dated Feb. 2, 2022, 20 pages.
Office Action issued in U.S. Appl. No. 16/094,754 dated Aug. 30, 2022, 20 pages.
Wikipedia, "Trocar", https://en.wikipedia.org/wiki/Trocar, downloaded Mar. 16, 2016, 2 pages.
Non Final Office Action for U.S. Appl. No. 16/094,754 dated Dec. 22, 2022, 11 pages.
Office Action for Japanese Application No. JP2021184037, dated Nov. 14, 2022, 6 pages.
Office Action for Chinese Application No. 201780037956.0, dated Nov. 24, 2022, 12 pages.
Final Office Action for U.S. Appl. No. 16/094,754 dated Apr. 13, 2023, 6 pages.
Huang et al. "A comprehensive study of low-power operation in IEEE 802.15. 4. In Proceedings of the 10th ACM Symposium on Modeling, analysis, and simulation of wireless and mobile systems" Oct. 23, 2007, pp. 405-408.
Notice of Reasons for Rejection dated Apr. 4, 2023 in Japanese Patent Application No. 2021-184037, with English Translation, 5 pages.
Office Action for Australian Application No. AU2022202336A1 dated May 12, 2023, 04 pages.

* cited by examiner

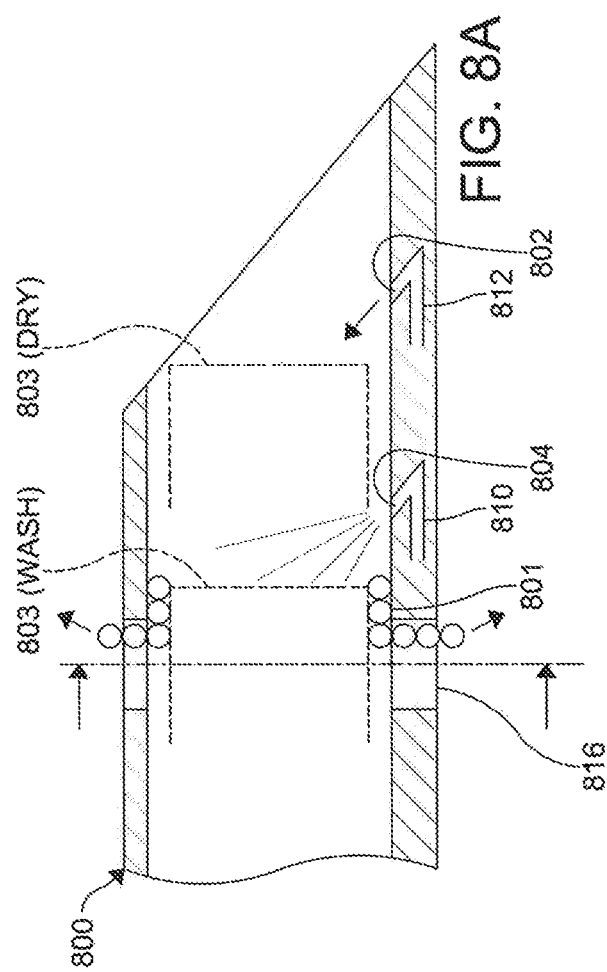
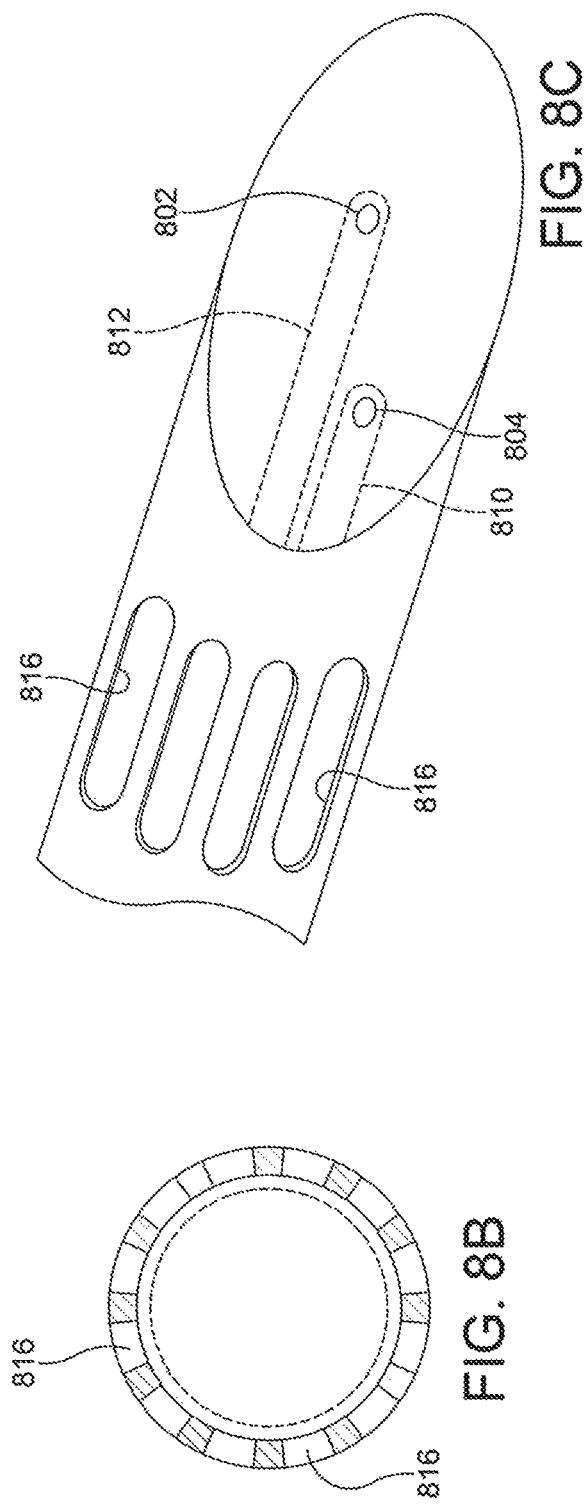

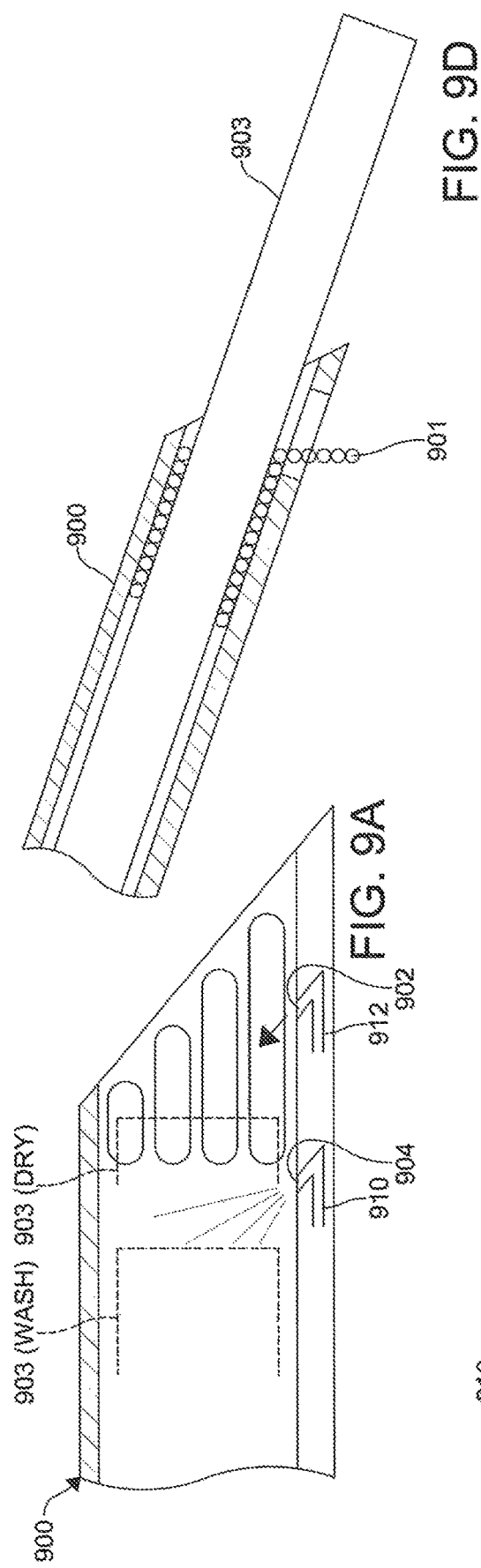
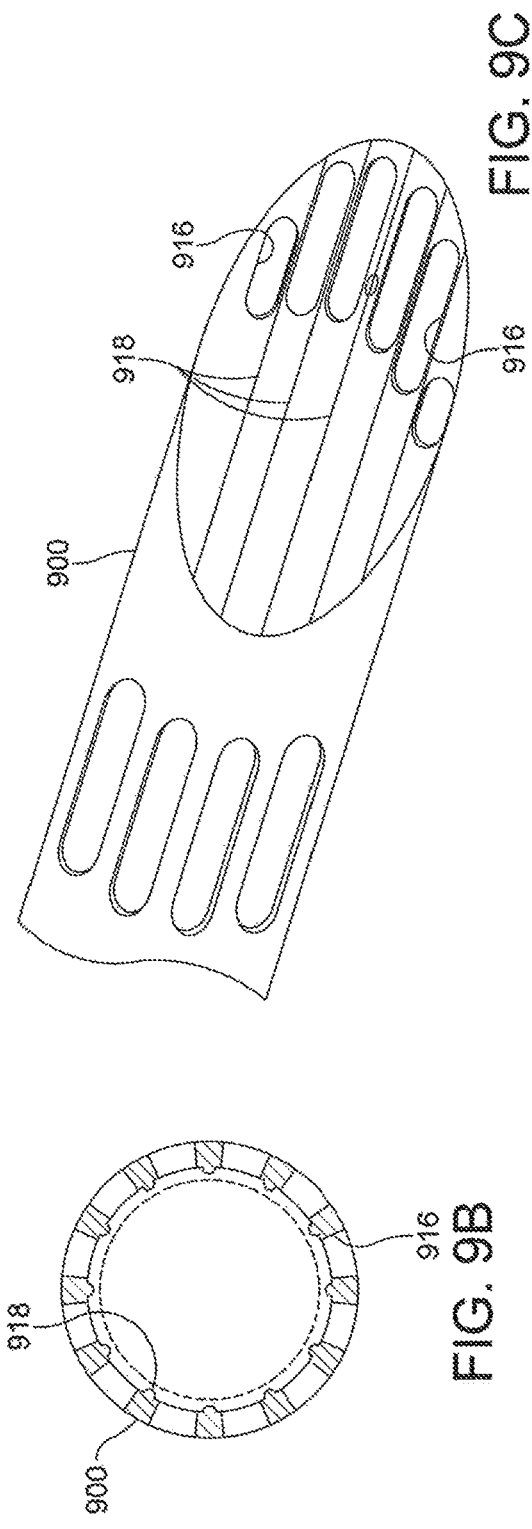

INTRAOPERATIVE ENDOSCOPE CLEANING SYSTEM

CROSS-REFERENCES TO OTHER RELATED PATENT APPLICATIONS

This patent application claims the benefit of U.S. Provisional Application Ser. No. 62/930,983, filed on Nov. 5, 2019.

BACKGROUND

1. Field of the Disclosure

The present disclosure generally relates to endoscopes, and more particularly to a system and method for maintaining a clean endoscope during a procedure.

2. Discussion of the Related Art

An endoscope is a medical device utilized for medical procedures requiring the visualization of internal organs in a non-surgical manner generally referred to as a minimally invasive procedure. A physician may utilize an endoscope to make a diagnosis and/or to gain access to internal organs for treatment. The endoscope may be introduced into a patient's body via a natural orifice or through a small surgical incision.

An endoscope generally comprises three systems; namely, the endoscope system, the imaging system and the illumination system. All three systems must work together to give the physician the entire, and clear picture. More specifically, in order to achieve optimal results, the physician must be able to have a clear view from insertion of the endoscope, traveling to the organ site and during the entire procedure. In order to do this, the lens of the endoscope must be maintained free and clear of any obstructing material, including smears, residue, debris and condensation without the need to remove the device from the body. Minimally Invasive Devices, Inc. has developed the FloShield™ system that directs carbon dioxide gas to the tip of the scope to clear the lens from condensation, debris and smoke. CIPHER SURGICAL has developed the OpClear® device which utilizes a gas-powered saline delivery system to clean the scope lens during a procedure.

While the above-referenced devices do function to clean endoscopes, these devices require additional components and are fairly complex in design and use thereof. For example, these devices comprise additional sleeves which are sized for particular endoscopes. For each endoscope, there is a sleeve and if a physician changes endoscopes during a procedure, which is a common occurrence, a new sleeve must also be utilized. In addition, these devices are fully manual device/systems which required the physician to perform additional steps and thus divert his or her attention from the primary task.

Accordingly, there exists a need for a simple, efficient and easy to utilize system and method for maintaining a clean scope lens and field of view.

SUMMARY OF THE DISCLOSURE

The present disclosure relates to a trocar for an intraoperative endoscope cleaning system. The trocar may comprise a main body comprising an elongate hollow tube portion extending terminating at a distal end, wherein the tube portion defines a cavity configured to receive an endoscope; a wash orifice disposed in the tube portion of the main body and configured to allow the wash solution to flow toward the cavity; a first gas orifice disposed in the tube portion of the main body between the wash orifice and the distal end of the main body, and configured to allow the pressurized gas to flow toward the cavity; and a second gas orifice disposed in the tube portion of the main body adjacent the wash orifice, and configured to allow the pressurized gas to flow toward the cavity and to atomize at least a portion of the wash solution in the cavity.

The present disclosure relates to a trocar for an intraoperative endoscope cleaning system. The trocar may comprise a main body comprising an elongate hollow tube portion extending terminating at a distal end, wherein the tube portion defines a cavity configured to receive an endoscope; a wash orifice disposed in the tube portion of the main body and configured to allow the wash solution to flow toward the cavity; a gas orifice disposed in the tube portion of the main body between the wash orifice and the distal end of the main body, and configured to allow the pressurized gas to flow toward the cavity; and a suction orifice disposed in the tube portion of the main body adjacent the wash orifice and configured to receive fluid from the cavity.

The present disclosure relates to a method for cleaning an endoscope during a procedure, the method comprising utilizing a trocar comprising a main body defining a cavity for receiving an endoscope, a wash orifice disposed in the main body and configured allow a flow of wash solution into the cavity, and a gas orifice disposed between the distal end of the main body and the wash orifice, the gas orifice configured allow a flow of gas into the cavity, the method comprising: washing the endoscope; drying the endoscope; and managing residual fluids on the endoscope or in the cavity, or both.

As a non-limiting example, the present disclosure describes improvements to the invention described in US20190125176A1 (prior art) for an endoscope cleaning system integrated into a trocar. The present disclosure describes solutions to a variety of problems that arise when the trocar design is reduced to practice and used in real world applications.

BRIEF DESCRIPTION OF THE DRAWINGS

The foregoing and other features and advantages of the disclosure will be apparent from the following, more particular description of preferred embodiments of the disclosure, as illustrated in the accompanying drawings.

FIGS. 8A-8C illustrate an example trocar comprising vents to mitigate against residual moisture.

FIG. 9A-9D illustrate an example trocar comprising drains and ribs to mitigate against residual moisture.

DETAILED DESCRIPTION OF THE PREFERRED EMBODIMENTS

The present disclosure is directed to a method and system for improving the efficiency of the spray at cleaning the scope. In the prior art the spray is created by delivering pressurized saline through an orifice. At low saline flow rates the spray energy reduces significantly to the point that the saline flows out of the nozzle in a stream rather than a spray. To overcome this and to enable the use of low flow rates the pressure of the saline can be increased, and the orifice diameter reduced however this adds complication to the system.

FIGS. 1A-1B illustrate an example trocar 100 for an intraoperative endoscope cleaning system. As shown, the trocar 100 may comprise a main body having an elongate hollow tube portion extending terminating at a distal end. The tube portion defines a cavity configured to receive an endoscope 114. A gas inlet port may be disposed through the main body and configured to selectively receive a pressurized gas (e.g., CO2). A fluid inlet port may be disposed through the main body and configured to selectively receive a wash solution. A wash orifice 104 may be disposed in the tube portion of the main body and in fluid communication with the fluid inlet port to receive the wash solution and to allow the wash solution to flow toward the cavity. A first gas orifice 102 may be disposed in the tube portion of the main body between the wash orifice 104 and the distal end of the main body, and in fluid communication with the gas inlet port to receive the pressurized and to allow the pressurized gas to flow toward the cavity. A second gas orifice 106 may be disposed in the tube portion of the main body adjacent the wash orifice 104, and in fluid communication with the gas inlet port to receive the pressurized gas and to allow the pressurized gas to flow toward the cavity and to atomize at least a portion of the wash solution in the cavity. A fluid channel 110 may be coupled between the fluid inlet port and the wash orifice 104 to provide fluid communication therebetween. A fluid channel 112 may be coupled between the gas inlet port and one or more of the first gas orifice 102 or the second gas orifice 106 to provide fluid communication therebetween.

Additionally or alternatively, and for the example purpose of controlling the delivery of the wash solution from the wash orifice 104 to the second gas orifice 106 it may be beneficial to create a recess or channel 108 connecting both ports 104, 106. In this way the solution from the wash orifice 104 is preferentially channeled to the gas orifice 106 for atomization into a spray. As shown in FIG. 1E, the trocar need not include the recess 108 shown in FIG. 1A.

In use, the endoscope 114A may be in a wash position and may be subjected to a spray of wash solution 105, which may be at least partially atomized by flow of gas 107. The endoscope 114B may be in a drying position and may be subjected to a burst of gas 103 for drying.

As shown in FIG. 10, a wash channel 110 may be coupled between the fluid inlet port and the wash orifice 104 to provide fluid communication therebetween and a gas channel 112 may be coupled between the gas inlet port and one or more of the first gas orifice 102 or the second gas orifice 106 to provide fluid communication therebetween, wherein at least a portion of the gas channel 112 is parallel to a portion of the wash channel 110. A recess 108' may have various shapes and may be formed adjacent or about one or more of the orifices 104, 106.

As shown in FIG. 1D, a wash channel 110 may be coupled between the fluid inlet port and the wash orifice 104 to provide fluid communication therebetween and a gas channel 112' coupled between the gas inlet port and one or more of the first gas orifice 102 or the second gas orifice 106 to provide fluid communication therebetween, wherein at least a portion of the gas channel 112' is shaped to surround at least a portion of the wash channel 110. Additionally or alternatively, a plurality of gas orifices (ports) 106A, 1066, 106C mat be disposed adjacent the wash orifice 104.

The gas orifices 106 may be connected to the drying gas fluid channel 112 to receive a flow of pressurized gas, for example. If a gas drying port 102 is activated concurrently with a wash solution (e.g., saline, buffered biocompatible solution, etc.) flow the additional gas port(s) 106 may be highly effective at atomizing the wash solution into an energetic spray. This offers a practical solution to creating energetic sprays at low saline pressures and flow rates. Another embodiment of this design uses a dedicated gas channel independent of the existing gas channel design. This has multiple benefits as the gas can be activated independently of the drying gas and be configured for the optimal gas pressure and flow rate to optimize the spray however this comes at an increase in the complexity of the system.

In the prior art, it was observed that the wash spray coalesces inside the trocar and has the potential to flow over the lower gas port. This typically occurs at the end of the washing cycle and thus the solutions flows over the gas drying port during the drying process resulting in a spray. In the present disclosure there is the same opportunity for the wash solution to coalesce inside the trocar and flow past the gas port during drying. This causes a spray which can compromise the drying stage of the clean as the CO2 gas has to run for an extended period to remove all the saline wash before the gas can effectively dry the scope.

In the present disclosure a solution to the problem is detailed which prevents any saline within the trocar from being atomized during drying. FIGS. 2A-2D illustrate an example trocar 200 for an intraoperative endoscope cleaning system. As shown, the trocar 200 may comprise a main body having an elongate hollow tube portion extending terminating at a distal end. The tube portion defines a cavity configured to receive an endoscope. A wash orifice 204 may be disposed in the tube portion of the main body. A gas orifice 202 may be disposed in the tube portion of the main body between the wash orifice 204 and the distal end of the main body. A fluid channel 210 may be coupled between the fluid inlet port and the wash orifice 104 to provide fluid communication therebetween. A fluid channel 212 may be coupled between the gas inlet port and one or more of the gas orifice 202 to provide fluid communication therebetween. The gas orifice 202 may have a raised elevation 224 relative to a surface 222 of the main body defining the cavity to prevent residual fluid 201 such as wash solution from washing up on to the gas orifice 202. Alternatively or additionally, channels 220 may be disposed adjacent the gas orifice 202 to divert the wash solution away from the gas orifice 202. Additionally or alternatively, a hydrophobic coating may be applied to the gas orifice 202 area to prevent wash from wicking up onto the port.

Figure 1:
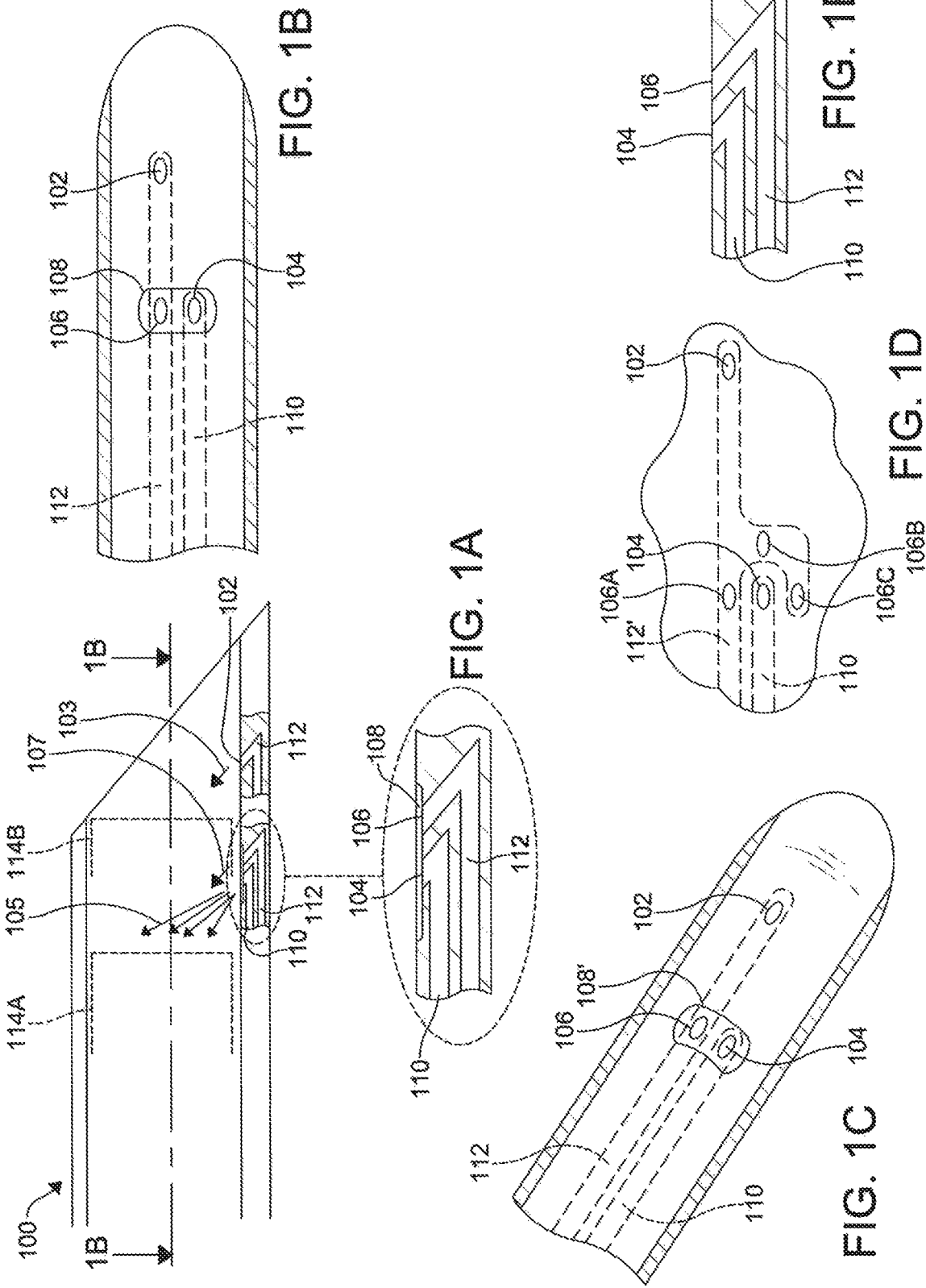
FIGS. 1A-1B are illustrations of an example trocar comprising a gas port (e.g., gas orifice) to atomize wash solution.
FIG. 1C is an illustration of an example trocar comprising a gas port (e.g., gas orifice) to atomize wash solution.
FIG. 1D is an illustration of an example trocar comprising a plurality of gas ports (e.g., gas orifice) to atomize wash solution.
FIG. 1E is an illustration of an example trocar without a recess adjacent the wash orifice and gas orifice.
Figure 2:
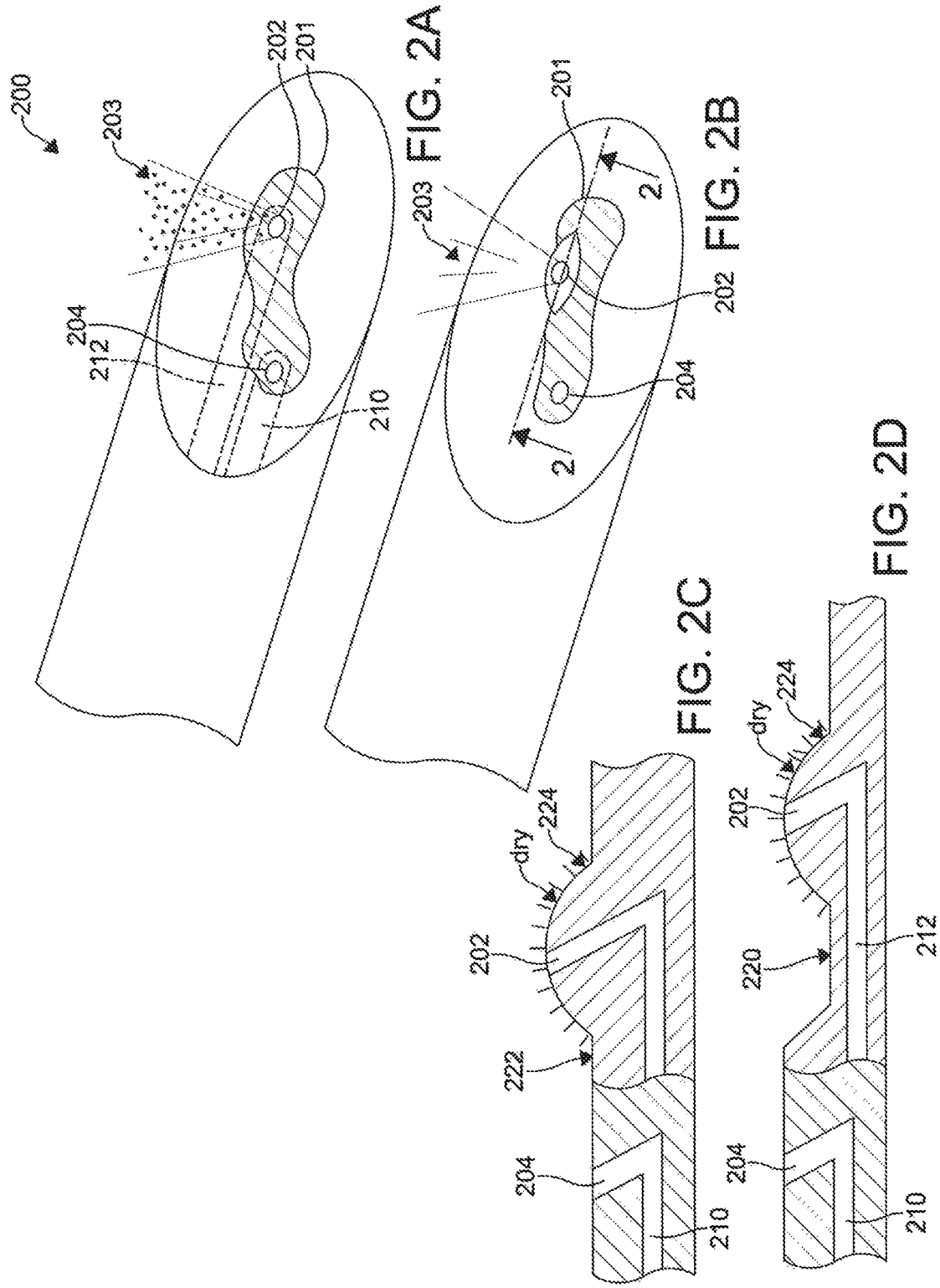
FIGS. 2A-2B illustrate example trocars showing residual fluid.
FIGS. 2C-2D illustrate example trocars comprising raised gas ports to prevent saline washing over the port and the generation of a mist during drying.
Figure 3:
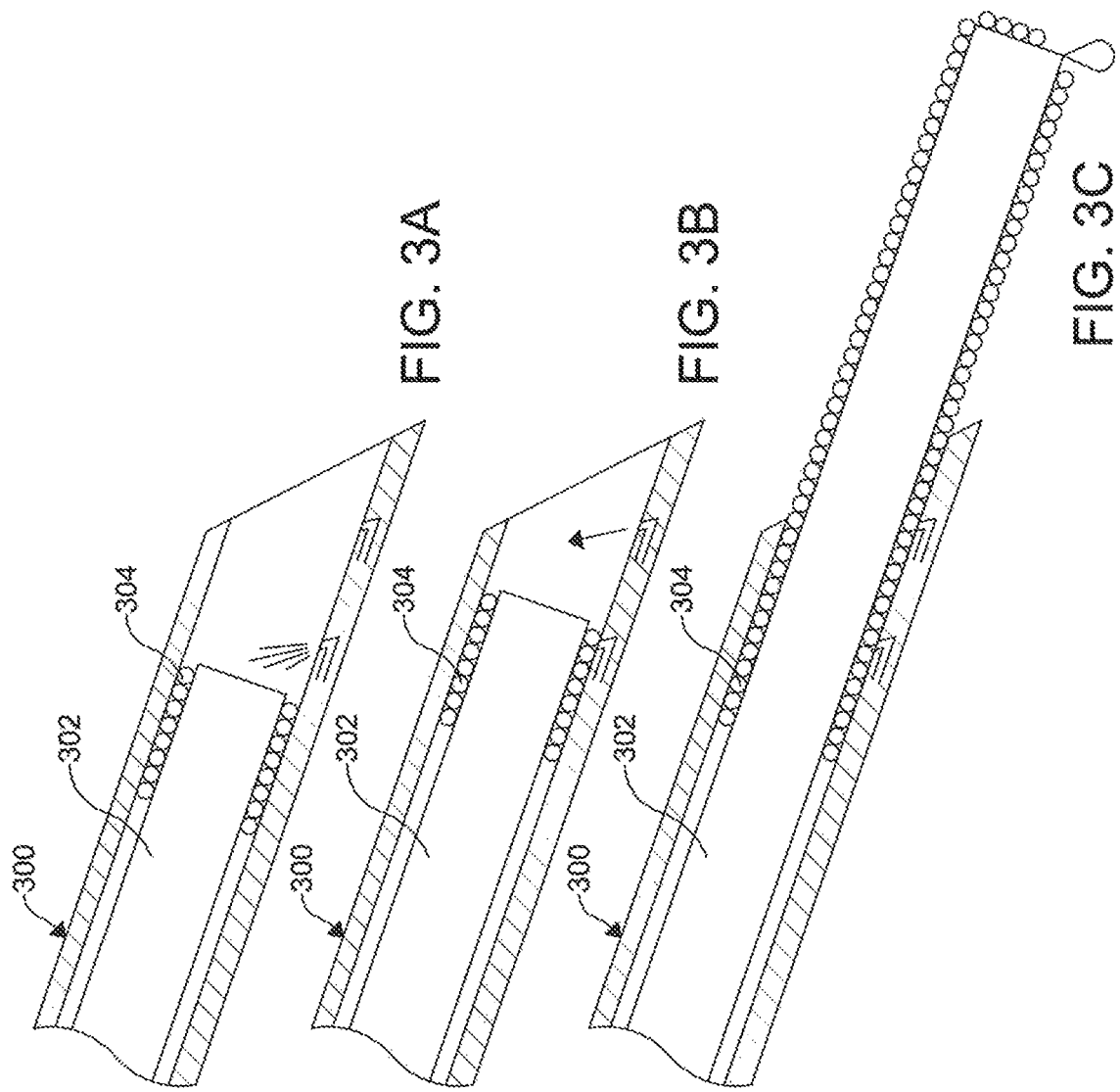
FIGS. 3A-3C illustrates an example problem of residual moisture and the resultant effect on the scope.

FIGS. 3A-3C illustrate examples of residual moisture. During washing and drying there is a propensity for wash solution 304 and/or other fluids fouling the scope e.g. blood to be pushed up the trocar 300 between the scope 302 and the walls of the trocar driven by the spray impingement and the high-pressure drying gas. When the cleaning cycle has ended ($CO_2$ gas turned off) the wash solution is under the influence of gravity and when the scope is tilted forward the solution runs down the scope and wets the scope window compromising the clean. Another cleaning cycle is then required to dry the scope.

Multiple solutions to the problem of residual moisture have been generated and evaluated.

Figure 4:
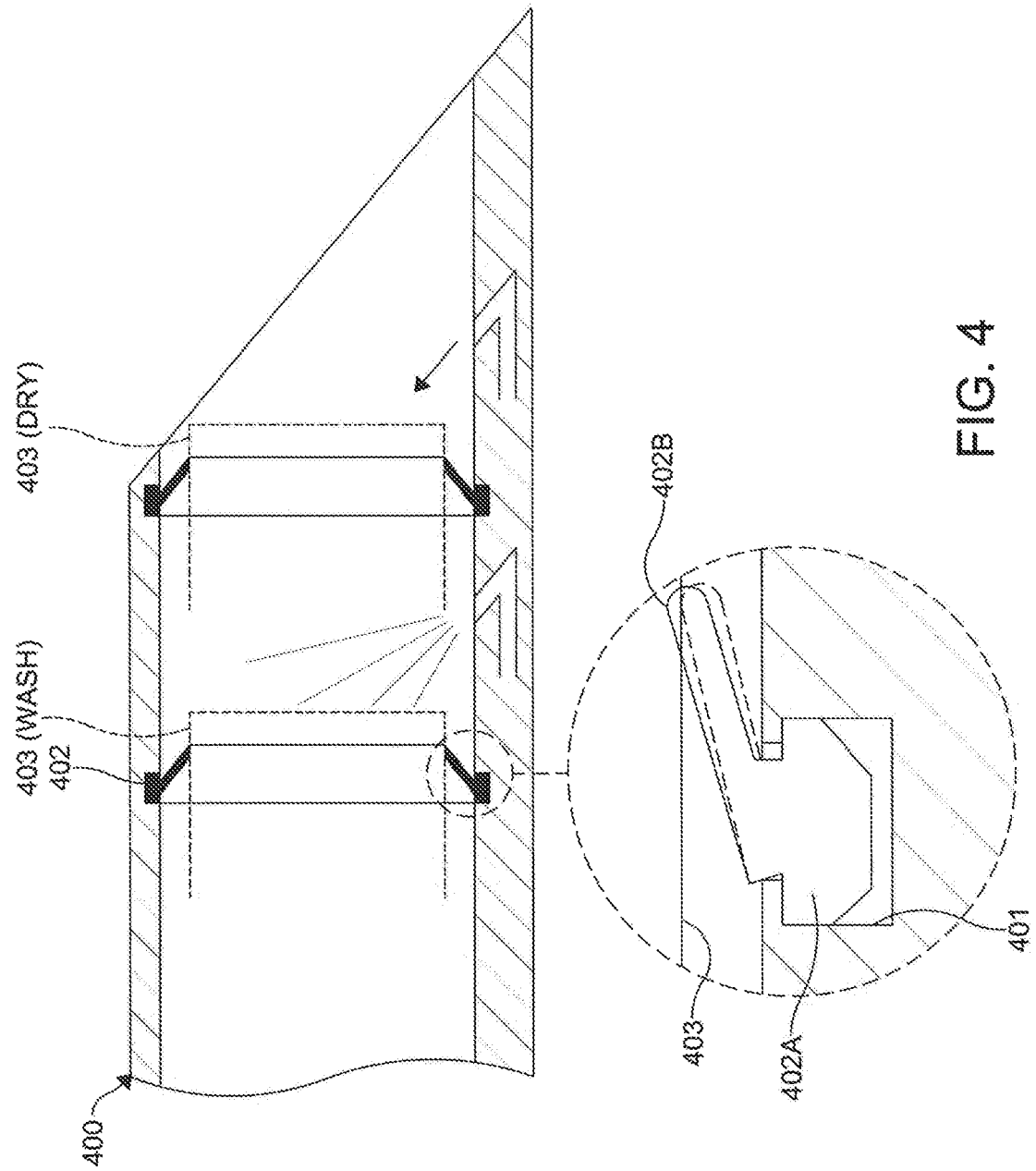
FIG. 4 illustrates an example trocar comprising physical seals to mitigate against residual moisture.

One solution comprises the use of physical seals within the trocar to compartmentalize the cleaning process. FIG. 4 shows an example of such a system. As shown in FIG. 4, two seals 402 have been used in the washing zone to prevent wash solution from a) going up into the trocar during washing (e.g., endoscope 403 in wash position) and b) flowing out of the trocar during the drying process (e.g., endoscope 403 in drying position). This solution has been shown to be highly effective at addressing the problem of residual moisture enabling an effective washing and drying cycle. As an example, lip seals were found to offer the sealing with low stiction. As a further example, a lip seal 402 may comprise a body 402A disposed in a cavity 401 formed in the wall of the trocar 400. A lip 402B may protrude from the body 402A and may extend toward the endoscope. Various design of seal angles, lip shapes and materials may be used.

Figure 5:
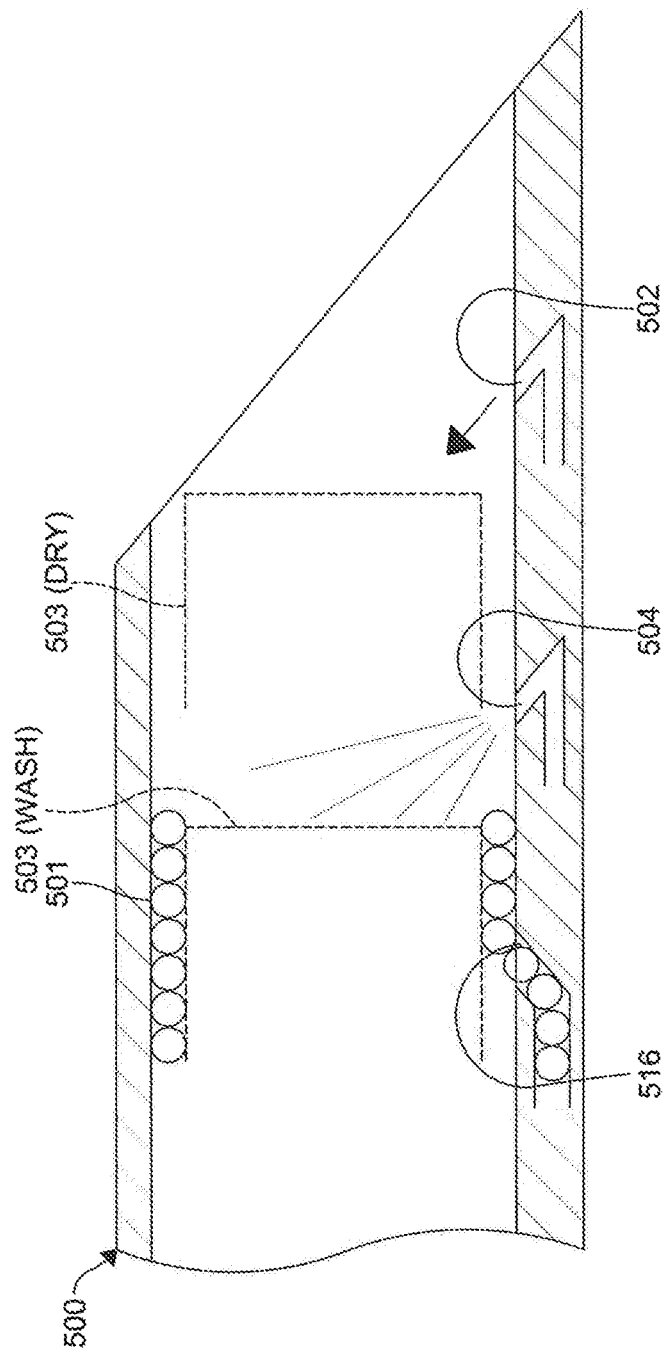
FIG. 5 illustrates an example trocar comprising suction to mitigate against residual moisture.

FIG. 5 shows a solution using a suction port 516 located proximally to a washing port 504. In this embodiment, the suction is activated during washing (endoscope 503 in wash position) and drying step (endoscope 503 in dry position) in the cleaning process and is highly effective at extracting moisture within the trocar 500 and removing the residual moisture 501. This solution also has the added benefit that the suction flow rate can be matched to the gas flow rate such that there is no net effect of the gas flow into the body cavity.

Figure 6A:
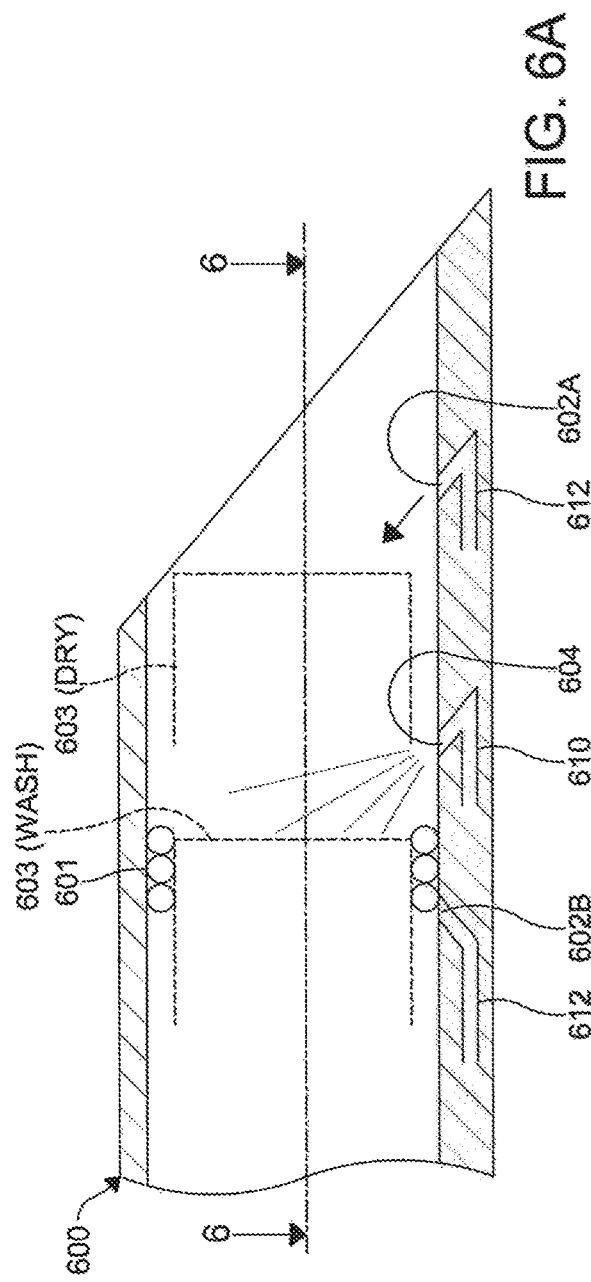
FIGS. 6A-6B illustrate an example trocar comprising rear gas pressure to mitigate against residual moisture.
Figure 6B:
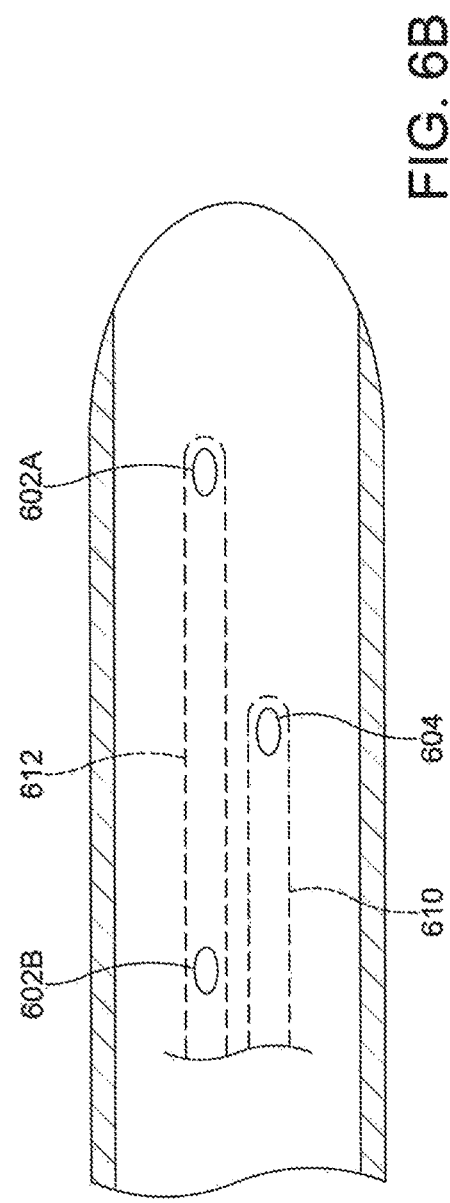

FIGS. 6A-6B shows a solution using an additional gas port 602B located proximally to the washing port 604. As shown, a gas channel 612 may provide pressurized gas to one or more gas ports 602A, 602B. A fluid channel 610 may provide wash solution to the washing port 604. In this embodiment the rear gas (e.g., via port 602B) is activated during washing (endoscope 603 in wash position) and drying (endoscope 603 in dry position). The rear gas creates a back pressure within the trocar which acts as a barrier preventing the ingress of saline 601 up the trocar 600. In this embodiment the flow of rear gas must be tightly controlled: too low and it is ineffective at preventing saline ingress and too high and it fights against the washing process to blow the spray away from the scope reducing the effectiveness of the wash. This control can be achieved in multiple ways however the simplest embodiment is controlling the orifice diameter, reducing the diameter to reduce the flow rate and vice versa. A more flexible solution would use a dedicated lumen supplying this orifice such that the gas pressure and flow rate can be set independently of the gas drying port.

Figure 7:
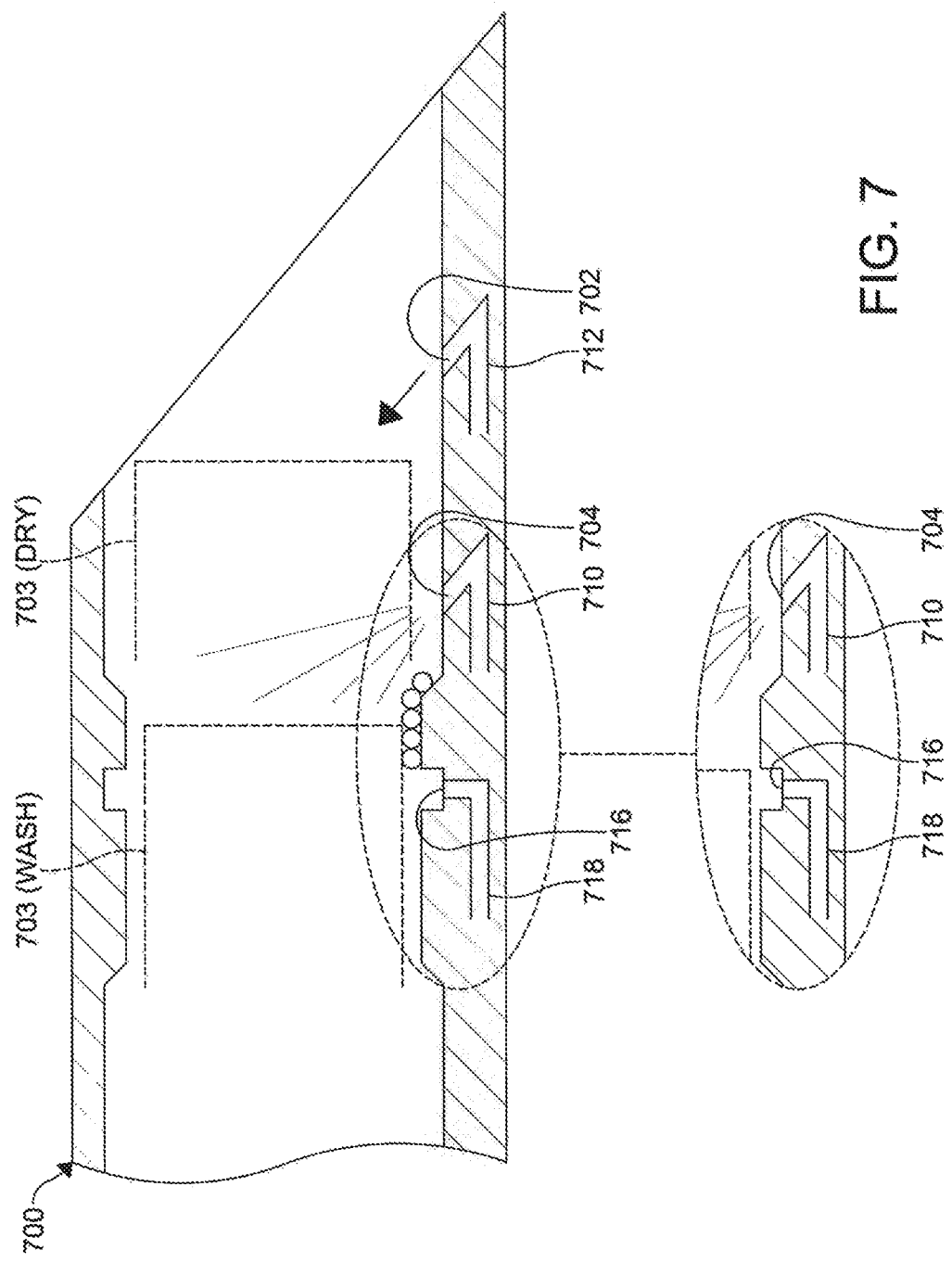
FIG. 7 illustrates an example trocar comprising a rear gas seal to mitigate against residual moisture.

FIG. 7 shows a rear gas pressure design. As shown, one or more gas channels 712, 718 may provide pressurized gas to one or more gas ports 702, 716. A fluid channel 710 may provide wash solution to the washing port 704. In this embodiment a reduction in the internal diameter of the trocar 700 is created and the rear gas port 716 is created in a groove such that within this location in such as position that the gas flow distally is higher than proximally. In this manner a gas seal can be created to prevent saline ingress using low gas flow rates and low pressures such that it doesn't compromise the effectiveness of the saline wash. In this embodiment the rear gas (e.g., via port 716) may be activated during washing (endoscope 703 in wash position) and drying (endoscope 703 in dry position).

FIGS. 8A-8C show an additional or alternative approach to dealing with residual moisture 801. As shown, a gas channel 812 may provide pressurized gas to one or more gas ports 802. A fluid channel 810 may provide wash solution to the washing port 804. As shown, vents 816 are created proximally in the trocar 800 to allow any wash solution and gas that passes beyond the scope 803 to be vented into the body cavity thus when the drying gas is turned off at the end of the drying step there is minimal moisture remaining in the trocar.

FIGS. 9A-9D show an additional or alternative approach to dealing with residual moisture 901. As shown, a gas channel 912 may provide pressurized gas to one or more gas ports 902. A fluid channel 910 may provide wash solution to the washing port 904. Drains 916 are created at the distal end of the trocar 900. These are designed to allow any residual moisture 901 within the trocar 900 to drain out of the trocar 900 rather than run down the length of the scope 903 to wet the scope lens. It may be beneficial that the scope is prevented from coming into contact with the walls of the trocar 900 as this increases the likelihood of wash wicking between the trocar and scope. To prevent this, ribs 918 are created axially within the inner surface of the trocar to position the scope centrally within the trocar thus creating channels that are effective are directing the residual moisture 901 to the drain.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated but should be constructed to cohere with all modifications that may fall within the scope of the appended claims. It is also noted that many of the above solutions are complementary such that more than one solution may be used at the same time to provide a more effective solution.

What is claimed is:

1. A trocar for an intraoperative endoscope cleaning system, the trocar comprising:
   a main body comprising an elongate hollow tube portion extending terminating at a distal end, wherein the tube portion defines a cavity configured to receive an endoscope;
   a wash orifice disposed in the tube portion of the main body and configured to allow the wash solution to flow toward the cavity;
   a gas orifice disposed in the tube portion of the main body between the wash orifice and the distal end of the main body, and configured to allow the pressurized gas to flow toward the cavity, the gas orifice including a raised elevation relative to an adjacent portion of a wall of the main body; and
   a fluid orifice disposed in the tube portion of the main body adjacent the wash orifice and configured to receive fluid from the cavity.

2. The trocar of claim 1, further comprising a fluid channel coupled between a fluid inlet port and the wash orifice to provide fluid communication there between.

3. The trocar of claim 1, further comprising a fluid channel coupled between a gas inlet port and the gas orifice to provide fluid communication there between.

4. The trocar of claim 1, further comprising a wash channel coupled between a fluid inlet port and the wash orifice to provide fluid communication therebetween and a gas channel coupled between a gas inlet port and the gas orifice to provide fluid communication therebetween, wherein at least a portion of the gas channel is parallel to a portion of the wash channel.

5. The trocar of claim 1, wherein the distal end of the tube portion of the main body comprises a shaped end having a first edge and a second edge opposite the first edge, wherein the first edge extends further from the head portion than the second edge.

6. The trocar of claim 1, wherein the wash orifice comprises an angled port formed through at least part of the tube portion of the main body.

7. The trocar of claim 1, wherein the gas orifice comprises an angled port formed through at least part of the tube portion of the main body.

8. The trocar of claim 1, further comprising one or more seals disposed adjacent the cavity and configured to seal against a portion of the endoscope while the endoscope is disposed in the cavity.

9. The trocar of claim 8, wherein the one or more seals comprise a lip seal.

10. The trocar of claim 8, wherein the one or more seals are disposed between the gas orifice and the wash orifice.

11. The trocar of claim 8, wherein the one or more seals are disposed adjacent the wash orifice and spaced from the gas orifice.

12. The trocar of claim 1, further comprising one or more vent apertures formed through the main body.

13. The trocar of claim 12, further comprising a protrusion formed on the main body and extending inwardly into the cavity, wherein the protrusion is disposed adjacent the one or more vent apertures.

14. An intraoperative endoscope cleaning system comprising:
    the trocar of claim 1;
    a control unit configured to control a flow of fluid to the trocar;
    a wash solution reservoir in fluid communication with the wash orifice; and
    a gas supply in fluid communication with the gas orifice.

15. The trocar of claim 1, wherein the gas orifice is a first gas orifice, and the trocar further comprises:
    a second gas orifice disposed in the tube portion of the main body adjacent the wash orifice and configured to allow the pressurized gas to flow toward the cavity and to atomize at least a portion of the wash solution in the cavity.

16. The trocar of claim 15, wherein the second gas orifice is configured to cause a higher gas flow distally than the gas flow proximally.

17. The trocar of claim 1, further comprising a wash channel coupled between a fluid inlet port and the wash orifice to provide fluid communication therebetween and a gas channel coupled between a gas inlet port and the gas orifice to provide fluid communication therebetween, wherein at least a portion of the gas channel is shaped to surround at least a portion of the wash channel.

18. The trocar of claim 17, further comprising one or more third gas orifices disposed in communication with the gas channel.

19. A method for cleaning an endoscope during a procedure, the method comprising utilizing a trocar, the trocar including:
    a main body comprising an elongate hollow tube portion extending terminating at a distal end, wherein the tube portion defines a cavity configured to receive an endoscope;
    a wash orifice disposed in the tube portion of the main body and configured to allow the wash solution to flow toward the cavity;
    a gas orifice disposed in the tube portion of the main body between the wash orifice and the distal end of the main body, and configured to allow the pressurized gas to flow toward the cavity, the gas orifice including a raised elevation relative to an adjacent portion of a wall of the main body; and
    a fluid orifice disposed in the tube portion of the main body adjacent the wash orifice and configured to receive fluid from the cavity;
    the method comprising:
    washing the endoscope;
    drying the endoscope; and
    managing residual fluids on the endoscope or in the cavity, or both.

20. The method of claim 19, wherein the managing residual fluids comprises using physical seals to compartmentalize the wash solution during the washing and drying phases of the method.

21. The method of claim 19, wherein the managing residual fluids comprises using suction to extract residual wash solution that ingresses the trocar during the washing and drying phases of the method.

22. The method of claim 19, wherein the managing residual fluids comprises using rear gas pressure to prevent wash solution ingress during the washing and drying phases of the method.

23. The method of claim 19, wherein the managing residual fluids comprises using a rear gas seal to prevent wash solution ingress during the washing and drying phases of the method.

24. The method of claim 19, wherein the managing residual fluids comprises using vents to passively allow wash solution to pass out of the trocar during the washing and drying phases of the method.

25. The method of claim 19, wherein the managing residual fluids comprises using drains and ribs to passively allow wash solution to pass out of the trocar during the washing and drying phases of the method.

* * * * *